United States Patent
Sugiyama et al.

(10) Patent No.: US 8,211,076 B2
(45) Date of Patent: Jul. 3, 2012

(54) DISPOSABLE DIAPER

(75) Inventors: Katsuhiko Sugiyama, Chuo-Ku (JP); Izumi Tashiro, Chuo-Ku (JP); Kahori Suzuki, Chuo-Ku (JP)

(73) Assignees: Oji Nepia Co., Ltd., Chuo-Ku (JP); Oji Paper Co., Ltd., Chuo-Ku (JP)

( * ) Notice: Subject to any disclaimer, the term of this patent is extended or adjusted under 35 U.S.C. 154(b) by 240 days.

(21) Appl. No.: 12/555,231

(22) Filed: Sep. 8, 2009

(65) Prior Publication Data

US 2009/0326505 A1     Dec. 31, 2009

Related U.S. Application Data

(62) Division of application No. 11/545,727, filed on Oct. 10, 2006, now Pat. No. 7,670,325.

(30) Foreign Application Priority Data

Oct. 14, 2005 (JP) ................................. 2005-300354
Aug. 3, 2006 (JP) ................................. 2006-211871

(51) Int. Cl.
  *A61F 13/15* (2006.01)
(52) U.S. Cl. ......... 604/385.28; 604/385.24; 604/385.25; 604/385.26
(58) Field of Classification Search ............. 604/385.28, 604/385.24, 385.25, 385.26
See application file for complete search history.

(56) References Cited

U.S. PATENT DOCUMENTS

| | | | |
|---|---|---|---|
| 5,575,782 | A | 11/1996 | Hasse et al. |
| 6,152,908 | A | 11/2000 | Widlund et al. |
| 6,508,798 | B1 | 1/2003 | Widlund et al. |
| 6,682,515 | B1 | 1/2004 | Mizutani et al. |
| 2004/0039363 | A1 | 2/2004 | Sugiyama et al. |

FOREIGN PATENT DOCUMENTS

| | | |
|---|---|---|
| GB | 2 268 073 | 1/1994 |
| JP | 04-99921 | 8/1992 |
| JP | 2559050 | 9/1997 |
| JP | 9-510385 | 10/1997 |
| JP | 3047219 | 1/1998 |
| JP | 11-347064 | 12/1999 |
| JP | 2000-342622 | 12/2000 |
| JP | 2001-145661 A1 | 5/2001 |
| JP | 2002-011044 | 1/2002 |
| JP | 2003-275247 | 9/2003 |

*Primary Examiner* — Jacqueline F. Stephens
(74) *Attorney, Agent, or Firm* — Burr & Brown

(57) ABSTRACT

A disposable diaper is provided, including an absorber, a top sheet disposed to cover an upper surface of the absorber and at least partially formed of a liquid permeable material, and a back sheet disposed to cover a lower surface of the absorber and formed of a liquid impermeable material. The disposable diaper further includes a skin contact sheet disposed above the top sheet and formed with a stool passing opening, which is an opening capable of passing a stool therethrough, and to the both sides of the skin contact sheet, at least a pair of standing gathers are formed, which are leakage prevention walls capable of standing three-dimensionally.

5 Claims, 7 Drawing Sheets

DISPOSABLE DIAPER

CROSS REFERENCE TO RELATED APPLICATIONS

This application is a division of U.S. application Ser. No. 11/545,727, filed Oct. 10, 2006, which claims the benefit of Japanese Application No. 2005-300354, filed Oct. 14, 2005 and Japanese Application No. 2006-211871, filed Aug. 3, 2006, the entireties of which are incorporated herein by reference.

BACKGROUND OF THE INVENTION

1. Field of the Invention

The present invention relates to a disposable diaper including an absorber, a top sheet, and a back sheet. The disposable diaper further includes a skin contact sheet which is disposed above the top sheet and formed with an opening capable of passing a stool therethrough.

2. Description of the Related Art

In recent years, as a diaper for an infant or an elder or disabled person, there has been a widely used a disposable diaper which includes an absorber, a top sheet disposed to cover the upper surface of the absorber and at least partially formed of a liquid permeable material, and a back sheet disposed to cover the lower surface of the absorber and formed of a liquid impermeable material. This disposable diaper is used in such a manner that a surface of the top sheet is applied to contact the skin of a wearer of the disposable diaper. Thereby, the urine discharged by the wearer penetrates through the top sheet and is absorbed and retained by the absorber. Further, the back sheet having good leakage preventing performance prevents the leakage of the excrement to the outside of the diaper.

In the disposable diaper of the above-described structure, however, the urine penetrates through the top sheet but most of the stool does not penetrate through the top sheet and thus remains thereon. The stool remaining on the top sheet adheres to the crotch or the buttocks of the wearer. This requires a troublesome wiping work which increases the burden of child rearing or nursing care, and also causes skin trouble to the wearer. Such phenomenon becomes more prominent when the stool discharged by the wearer is an unformed stool.

In view of this, another type of disposable diapers has been proposed in which another sheet member (hereinafter referred to as a "skin contact sheet" in the present specification) is disposed above the top sheet (see Paragraph 0010 and FIG. 2 of Japanese Registered Utility Model No. 2559050, and Paragraph 0020 and FIG. 1 of Japanese Unexamined Patent Application Publication No. 2002-11044, for example). These disposable diapers are structured such that the skin contact sheet is formed with an opening capable of passing the stool therethrough (i.e., a stool passing opening) for causing the stool discharged by the wearer to drop on the top sheet through the stool passing opening.

According to the above-described disposable diaper, the skin contact sheet first contacts the skin of the wearer. Thus, the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer can be expected.

However, in the disposable diaper having the skin contact sheet, as compared with known disposable diapers, leakage from leg-surrounding openings and the like of the diaper (i.e., the so-called sideward leakage) easily occurs. That is, the disposable diaper is not satisfactory enough in the prevention of the sideward leakage of urine, and thus is still open to improvement.

SUMMARY OF THE INVENTION

As described above, a disposable diaper in which the discharged stool does not easily contact with the skin of the wearer and capable of effectively preventing the sideward leakage of urine has not yet been disclosed so far, and thus has been longed for. In view of the conventional techniques as described above, it is an object of the present invention to provide a disposable diaper in which the discharged stool does not easily contact with the skin of the wearer and capable of effectively preventing the sideward leakage of urine.

The present inventors conducted a keen examination to improve the above-described conventional techniques and obtained a finding that, in the disposable diaper having the skin contact sheet, urine is sometimes discharged on the skin contact sheet. In such a case, because the urine diffuses down the skin contact sheet, the sideward leakage of the urine tends to occur. Then, to solve the above-described disadvantages, in addition to providing the skin contact sheet, the present inventors has been made with the idea of forming at least a pair of standing gathers to both sides of the skin contact sheet. Specifically, the present invention provides the following disposable diaper.

A disposable diaper according to a first aspect of the present invention includes an absorber, a top sheet disposed to cover an upper surface of the absorber and at least partially formed of a liquid permeable material, and a back sheet disposed to cover a lower surface of the absorber and formed of a liquid impermeable material. The disposable diaper further includes a skin contact sheet disposed above the top sheet and formed with a stool passing opening, which is an opening capable of passing a stool therethrough, and to the both sides of the skin contact sheet, at least a pair of standing gathers which are leakage prevention walls capable of three-dimensionally standing is formed.

According to a second aspect of the present invention, in the disposable diaper according to the first aspect of the present invention, the standing gathers are formed with folded parts of side edges of the skin contact sheet and integrally formed with the skin contact sheet.

According to a third aspect of the present invention, in the disposable diaper according to the first or second aspect of the present invention, the standing gathers are formed along both side edges of the skin contact sheet.

According to a fourth aspect of the present invention, in the disposable diaper according to either one of the first to third aspects of the present invention, the standing gathers are formed that upper end edges of the standing gathers are disposed to positions higher than a surface of the skin contact sheet.

According to a fifth aspect of the present invention, in the disposable diaper according to either one of the first to fourth aspects of the present invention, the standing gathers' lower end edges are disposed on the surface of the skin contact sheet.

In the disposable diaper according to the present invention, the discharged stool does not easily directly contact with the skin of the wearer and the disposable diaper is capable of effectively preventing the sideward leakage of urine. That is, the disposable diaper according to the present invention is excellent in preventing the disadvantage (sideward leakage of urine) due to the provision of the skin contact sheet while retaining the advantage of the provision of the skin contact sheet. Incidentally, the word "standing gather(s)" may be expressed as "barrier cuff".

DETAILED DESCRIPTION OF THE INVENTION

Specific description will now be made of preferred embodiments of the disposable diaper according to the present invention, taking a two-piece-type and pants-type diaper as an example. The present invention, however, widely includes disposable diapers which have particular features of the invention, and thus is not limited to the following embodiments. For drawing convenience, leg-surrounding stretchable members are eliminated from FIG. 3 to FIG. 7.

Figure 1:
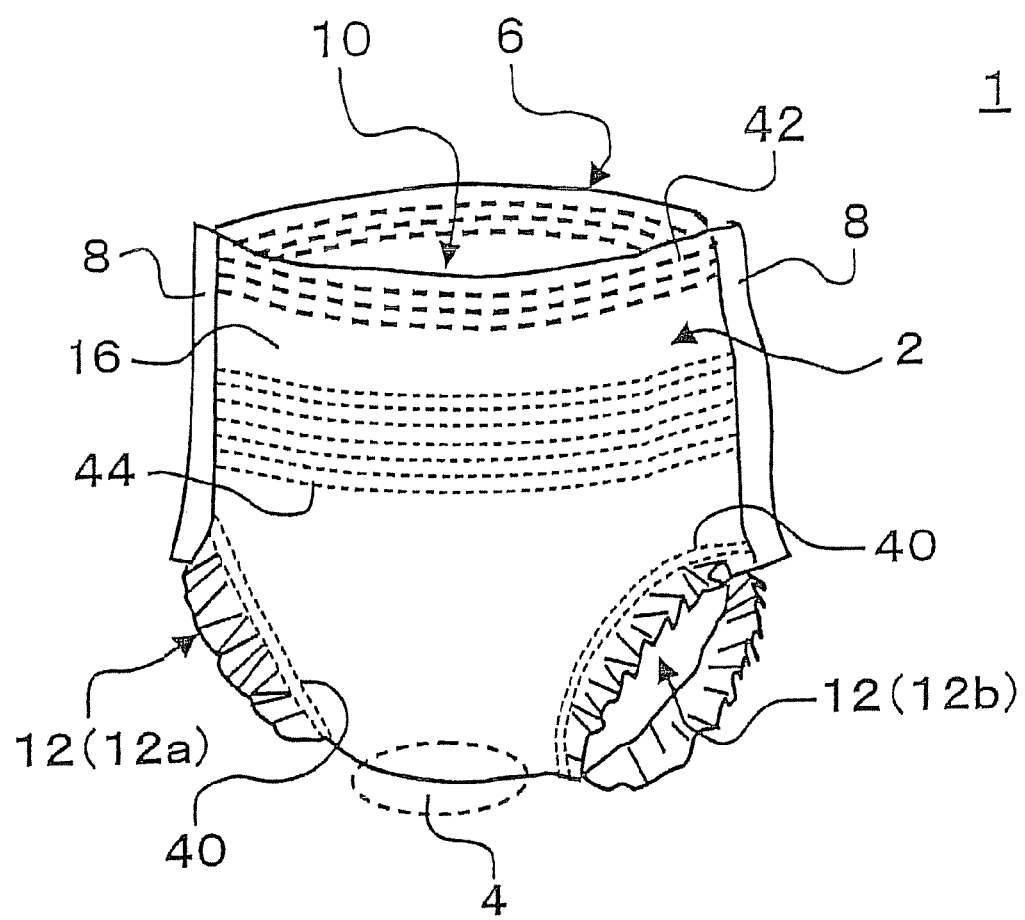
FIG. 1 is a schematic perspective view illustrating one embodiment of the disposable diaper according to the present invention, as viewed from the front side of the diaper.
Figure 2:
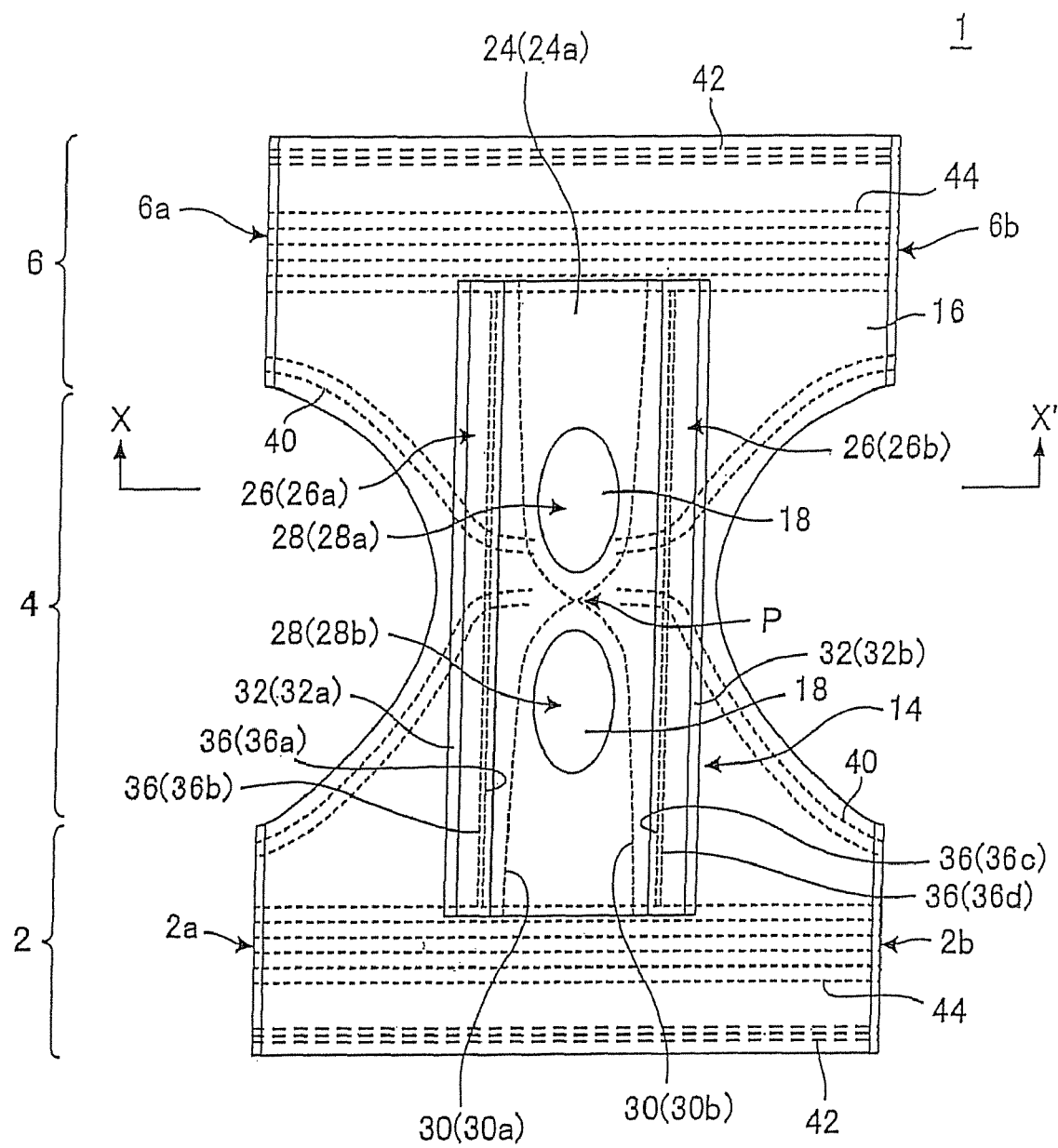
FIG. 2 is a plan view illustrating the one embodiment of the disposable diaper according to the present invention, as viewed from the side of the absorbent member of the disposable diaper when the diaper shown in FIG. 1 is unfolded.
Figure 3:
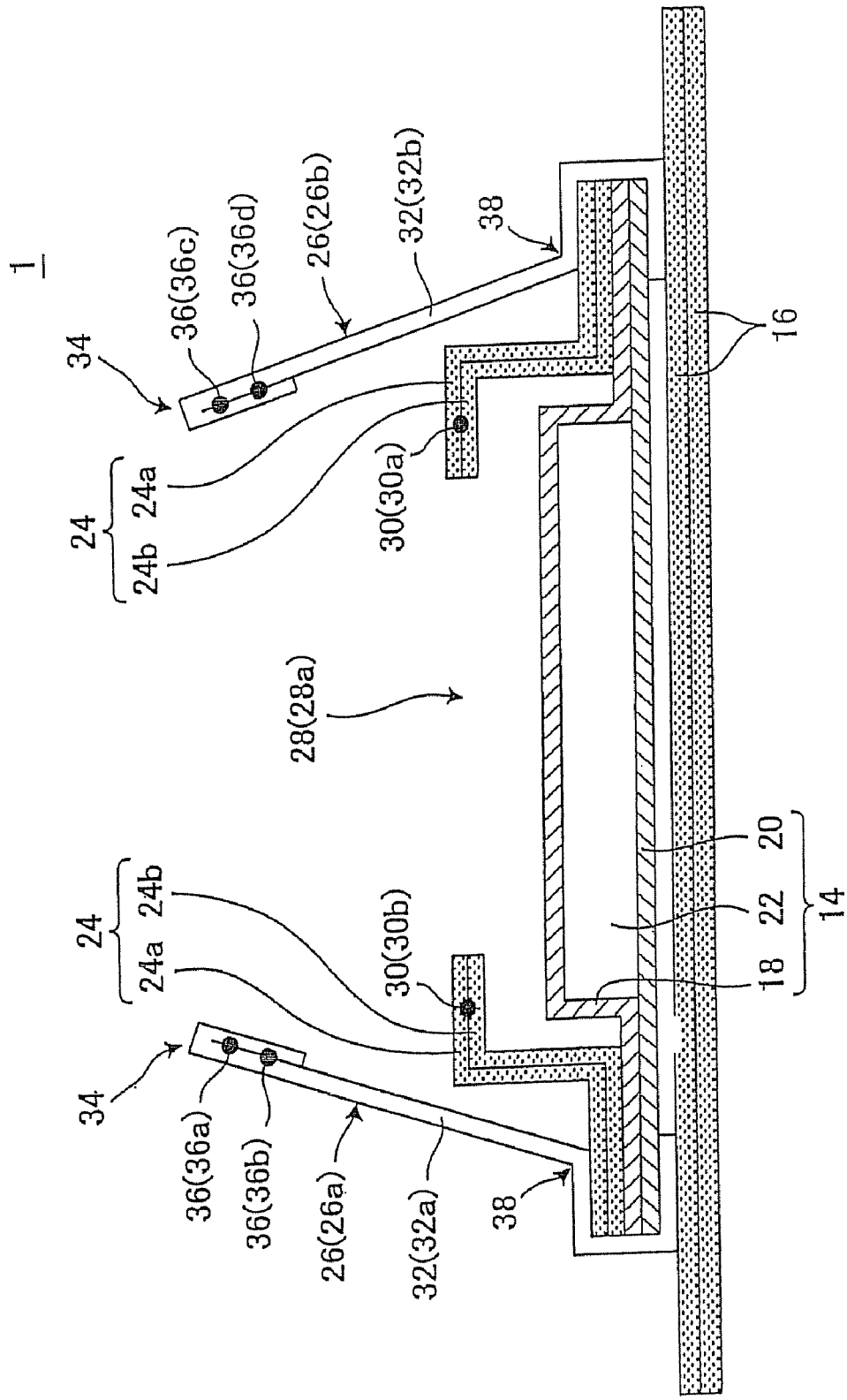
FIG. 3 is a schematic cross-sectional view illustrating the one embodiment of the disposable diaper according to the present invention, as cut along the X-X' line in the disposable diaper shown in FIG. 2.

In the present specification, the phrase "pants-type diaper" refers to a diaper preformed into a pants shape, as in the case of a disposable diaper 1 illustrated in FIGS. 1 and 2, in which corresponding side edges of a front body part 2 and a back body part 6 (i.e., side edges 2a and 6a and side edges 2b and 6b) are joined together to form joining parts 8, a waist-surrounding opening 10, and a pair of leg-surrounding openings 12a and 12b. Further, the phrase "two-piece-type diaper" refers to a type of diaper which includes an absorbent member 14 having a function of absorbing and retaining the excrement of a wearer of the diaper (i.e., an absorbing and retaining function) and an exterior covering member 16 having a function of covering the body of the wearer (i.e., a fitting function), and in which the absorbent member 14 is disposed on the inside of the exterior covering member 16. As illustrated in FIG. 3, the absorbent member 14 is a member including, as component parts thereof, an absorber 22, a top sheet 18, and a back sheet 20.

Further, in the present specification, the phrase "front body part," refers to a part covering the ventral part (i.e., the front side of the body) of a wearer when the diaper is applied to the wearer, the phrase "crotch part," refers to a part covering the crotch of a wearer when the diaper is applied to the wearer, and the phrase "back body part" refers to a part covering the dorsal part (i.e., the back side of the body) of a wearer when the diaper is applied to the wearer, respectively.

[1] The structure of the disposable diaper according to the present invention: As in the case of the disposable diaper 1 illustrated in FIGS. 1 to 3, the disposable diaper according to the present invention is a disposable diaper including the absorber 22, the top sheet 18, and the back sheet 20. The disposable diaper further includes a skin contact sheet 24 which is disposed above the top sheet 18 and is formed with an opening capable of passing the stool therethrough (i.e., a stool passing opening 28a). To the both sides of the skin contact sheet 24, at least a pair of standing gathers 26 (26a and 26b) which are leakage prevention walls structured to stand three-dimensionally is formed.

[1-1] The skin contact sheet: The skin contact sheet is a member for separating the skin of the wearer from the top sheet, and is a sheet-shaped member disposed above the top sheet and formed with an opening capable of passing the stool therethrough (i.e., a stool passing opening). With the provision of the skin contact sheet, the skin of the wearer first contacts the skin contact sheet, and thus the top sheet disposed under the skin contact sheet does not easily come into direct contact with the skin of the wearer. That is, the skin of the wearer is separated from the top sheet. This also means that a shielding layer, i.e., the skin contact sheet, intervenes between the top sheet and the skin of the wearer. Therefore, even if the stool remains on the top sheet, the effect of substantially decreasing the chance of direct contact of the stool with the skin of the wearer is obtained.

As the material forming the skin contact sheet, for example, a nonwoven fabric, a mesh sheet, a film, or the like made of such a resin as polyethylene, polypropylene, and polyester can be used. In particular, it is preferable to use the nonwoven fabric for the good texture against the skin. The above-described materials may be liquid permeable, liquid impermeable, or water repellent. It is preferable, however, that the above-described materials are water repellent materials (e.g., a water repellent nonwoven fabric) for the ability to maintain a dry texture (i.e., dryness) even after a long time wearing.

The skin contact sheet of the disposable diaper according to the present invention needs to be formed with the opening capable of passing therethrough the stool discharged by the wearer (i.e., the stool passing opening). With this structure, the stool discharged by the wearer drops on the top sheet through the skin contact sheet, and thus the chance of direct contact of the stool with the skin of the wearer can be substantially decreased.

There is no particular restriction on the shape of the stool passing opening, as long as the shape allows the passage of the stool. That is, the "opening" capable of passing the stool therethrough includes the so-called opening (i.e., a hole) such as a circular opening, an oval opening, and a rhombic opening, and also includes a slit such as a straight-line slit, a cross-shape slit, and a star-shape slit formed by crossing three or more slits. Specifically, the oval opening, or the star-shape slit in which an anteroposterior direction (longitudinal direction) of the diaper is a long axis direction is preferable. The oval opening has an advantage that the stool can easily pass through the opening of the skin contact sheet, and the star-shape slit has an advantage of effectively preventing that the stool once passed through the opening of the skin contact sheet and dropped onto the top sheet exposes again from the opening of the skin contact sheet and contaminate the buttocks of the wearer. For example, the disposable diaper 1 illustrated in FIG. 2 is an example of a disposable diaper on which an oval opening whose anteroposterior direction is the long axis direction is formed to the part corresponding to a crotch part 4 of the skin contact sheet 24 as the stool passing opening 28*a*. Sizes of the hole and slit can be appropriately decided in consideration of the function of "passing the stool".

The skin contact sheet may be formed with a urine passing opening to a region toward the front body side from the stool passing opening. That is, it is preferable that the skin contact sheet is formed with the stool passing opening and the urine passing opening, as the openings.

With the formation of the urine passing opening as described above, it is possible to cause the urine discharged by the wearer to securely flow into the inside of the skin contact sheet through the opening. Thereby, it is possible to effectively prevent the urine from diffusing down the skin contact sheet and leaking sideward from the leg-surrounding openings and the like of the diaper. For instance, the disposable diaper 1 illustrated in FIG. 2 is an example in which, in addition to the stool passing opening 28*a* of the oval shape, a urine passing opening 28*b* of an oval shape is further formed on the skin contact sheet 24 as the opening 28. In this example, the stool passing opening 28*a* is formed at a portion corresponding to the crotch part 4 of the disposable diaper 1, and the urine passing opening 28*b* is formed at a portion toward the front body part 2 from the stool passing opening 28*a*.

In the case in which two openings (i.e., the stool passing opening and the urine passing opening) are formed as in the above-described case, it is preferable to provide a separation wall for dividing the space between the skin contact sheet and the top sheet into a space communicating with the stool passing opening and a space communicating with the urine passing opening.

If the urine and the stool are mixed, ammonia is generated and alkalinizes the surrounding environment. Then, an enzyme included in the stool is strongly activated in an alkaline atmosphere, and the enzyme and ammonia inflame a weakened part of the skin. Thereby, the diaper rash occurs. This mechanism is reported by Kazuya Yamamoto in Hifu Rinsho (Clinical Dermatology) 1998, vol. 30, pp 949-956. With the provision of the above-described separation wall, the urine discharged by the wearer can be absorbed and retained separately from the stool. As a result, the urine and the stool are not easily mixed, and the diaper rash can be effectively prevented.

It is preferable that a stretchable member (i.e., an opening stretchable member) is placed around the outer periphery of the opening. With the provision of the opening stretchable member, the skin contact sheet is applied with tension and thus becomes elastic. This contributes to an advantage that the skin contact sheet can be prevented from being crushed and sinking toward the top sheet, and that the skin contact sheet can easily come into contact with the skin of the wearer. Further, with the provision of the opening stretchable member, it is possible to generate force for causing the skin contact sheet to contract and causing the top sheet, the absorber, and the back sheet to bend toward the downside (i.e., toward the exterior covering member). Therefore, the skin contact sheet can be kept spaced from the top sheet, and the skin contact sheet and the top sheet can be definitely separated from each other.

As the material for the opening stretchable member, stretchable materials used in conventional disposable diapers can be preferably used. Specifically, the material may be a rubber thread or a flat rubber string made of a natural rubber or a synthetic rubber (e.g., urethane rubber), a stretchable net, a stretchable film, stretchable foam (e.g., urethane foam), or the like.

There is no particular restriction on the arrangement pattern of the opening stretchable member, as long as the pattern allows the exertion of the above-described effects. To definitely apply the stretching force to the opening, however, it is preferable that the opening stretchable member is arranged in such a pattern to surround the peripheral rim of the opening. For example, it is preferable to arrange the opening stretchable member in such a pattern as a circular pattern, an oval pattern, or a rhombic pattern to surround the peripheral rim of the opening.

In another preferable embodiment, two opening stretchable members are used as the opening stretchable members and arranged in such a pattern to cross at least one point anterior or posterior to the opening so as to surround a part of the peripheral rim of the opening. With the opening stretchable members arranged in such a pattern, the opening stretchable members can be continuously arranged in the anteroposterior direction of the diaper. This is preferable in view of the advantage that the continuous manufacture of disposable diapers can be easily performed.

For example, the disposable diaper 1 illustrated in FIG. 2 is an example in which two opening stretchable members 30*a* and 30*b* are used as the opening stretchable members 30 and arranged in such a pattern to cross at a point P between the stool passing opening 28*a* and the urine passing opening 28*b* so as to surround a part of the peripheral rim of each of the stool passing opening 28*a* and the urine passing opening 28*b*. With the opening stretchable members 30*a* and 30*b* arranged in such a pattern, it is possible to easily manufacture an absorbent member continuum in which the absorbent member 14 is continuously arranged in the longitudinal direction.

Further, in the disposable diaper 1 illustrated in FIG. 2, the opening stretchable members 30*a* and 30*b* are arranged to cross at the center of the crotch part 4. With this arrangement, the stretching force in the width direction (i.e., the sideward direction of the diaper) can be applied more at the crotch part 4 (i.e., the proximity of the point P) than at the front body part 2 or the back body part 6 of the diaper. Therefore, there is an effect of making the skin of the wearer come into closer contact with a portion of the skin contact sheet 24 between the stool passing opening 28*a* and the urine passing opening 28*b*, which tends to sag with relative ease. Furthermore, in the disposable diaper 1 illustrated in FIG. 2, the opening stretchable members 30*a* and 30*b* do not cross at other points than the center point P of the crotch part 4. Thus, the opening stretchable members 30*a* and 30*b* are arranged in such a pattern that a part of the peripheral rim of the stool passing opening 28*a* at the side of the back body part 6 and a part of the peripheral rim of the urine passing opening 28*b* at the side of the front body part 2 are open. With this arrangement, portions of the skin contact sheet 24 at the sides of front body part 2 and the back body part 6 do not come into excessively close contact with the skin of the wearer, and thus the breathability can be ensured. Accordingly, perspiration due to the contact of the skin contact sheet is suppressed, and the stuffiness and the skin trouble attributable to the sweat can be effectively prevented.

The opening stretchable member as described above is fixed to the skin contact sheet with an adhesive agent or another medium. The method of fixing the opening stretchable member may be bonding with a hot-melt adhesive agent or another adhesive agent of high fluidity, or welding with heat or ultrasound such as heat-sealing, for example.

To apply sufficient stretching force to the opening, it is preferable to fix the opening stretchable member with the opening stretchable member stretched. For example, if the opening stretchable member is a natural rubber or a synthetic rubber, it is preferable to fix the opening stretchable member with the opening stretchable member stretched by 100 to 400%, and more preferably by 200 to 300%. With the opening stretchable member fixed with the stretching rate of the above range, it is possible to apply the sufficient stretching force to the opening and to prevent the opening from unnecessarily contracting.

There is no particular restriction on the method of arranging the opening stretchable member. However, as in the case of the disposable diaper 1 illustrated in FIG. 3, for example, it is preferable to form the skin contact sheet 24 by pasting together two sheet members (i.e., an upper sheet 24a and a liner sheet 24b), and to place the opening stretchable members 30a and 30b to be sandwiched between the upper sheet 24a and the liner sheet 24b. The use of this arrangement method is preferable in that the stretching force can be applied to the skin contact sheet by the minimum necessary stretchable members.

When the above-described structure is employed, it is enough if the portion of the skin contact sheet where the opening stretchable members are placed is formed with two sheet members, and it is not necessary that the whole of the skin contact sheet is formed with the two sheet members. For example, in a disposable diaper 90 illustrated in FIG. 7, a portion where the opening stretchable members 30a and 30b are placed is formed with the two sheet members (i.e., the upper sheet 24a and the liner sheet 24b) and other parts are parts are formed with one sheet member (the upper sheet 24a).

Figure 7:
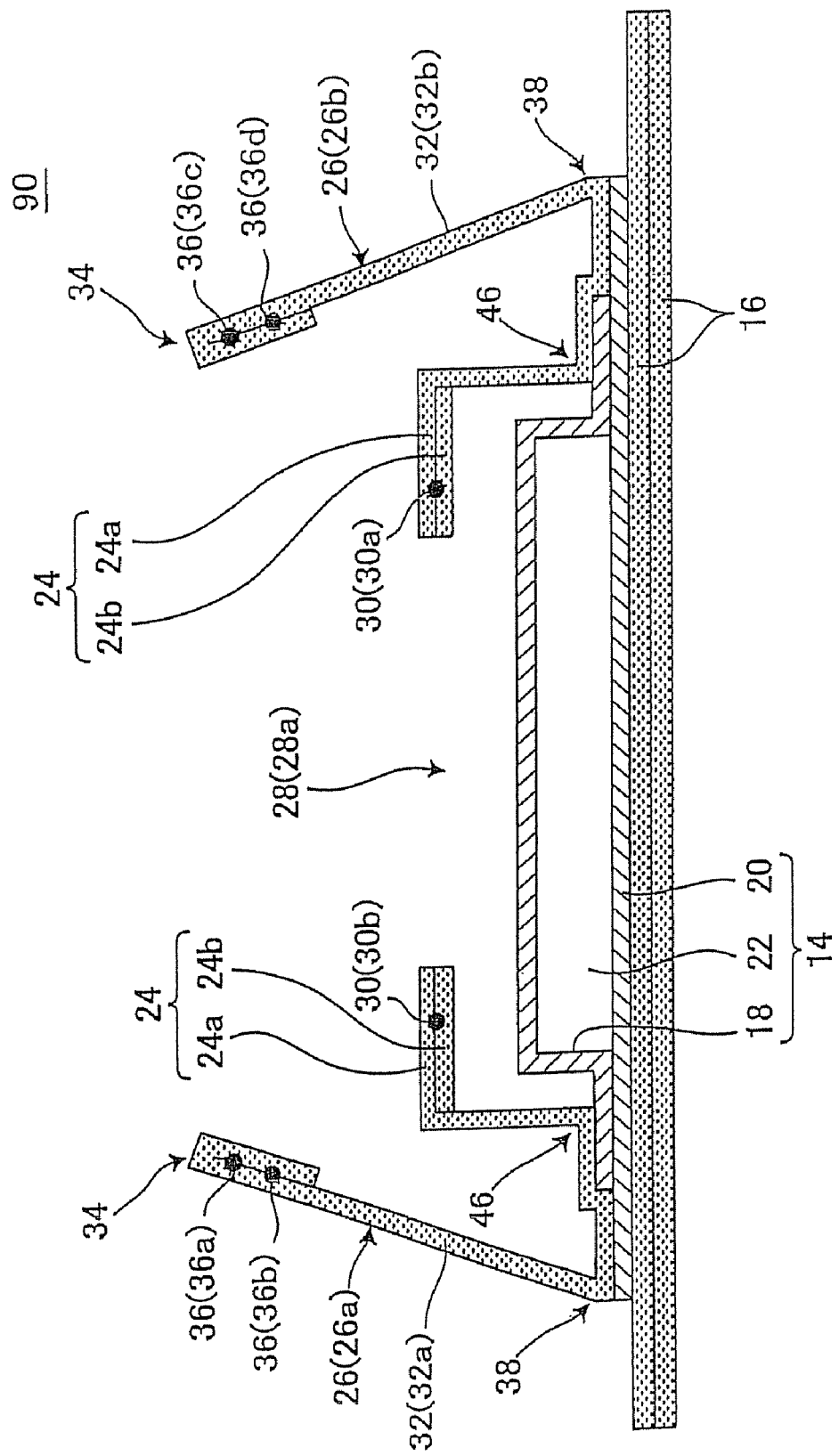
FIG. 7 is a schematic cross-sectional view illustrating still yet another embodiment of the disposable diaper according to the present invention, as cut the disposable diaper according to the present invention at the part of the stool passing opening in the width direction.

With the above-described structure, a portion standing from a standing line 46 of the skin contact sheet 24 is formed with only one sheet member (i.e., the upper sheet 24a), as compared with the case in which the portion is formed with two sheet members, the portion standing from the standing line 46 becomes soft and flexible. Accordingly, there are advantages that the skin contact sheet 24 easily stands to fit the shape of the skin of the wearer (i.e., the portion of the crotch), easily come into close contact, and good fitteness can be obtained. Therefore, original effect of the skin contact sheet significantly contributes. The disposable diaper 90 illustrated in FIG. 7 is an example of a diaper formed such that the liner sheet 24b is formed to have narrow width and with the upper sheet 24a which has a wide width protruding from the liner sheet 24b which has the narrow width, standing gathers 26a and 26b are formed. On the contrary, similar effect can be obtained even if the upper sheet is formed to have a narrow width and with a liner sheet which has a wide width protruding from the upper sheet having the narrow width, the standing gathers are formed.

Figure 4:
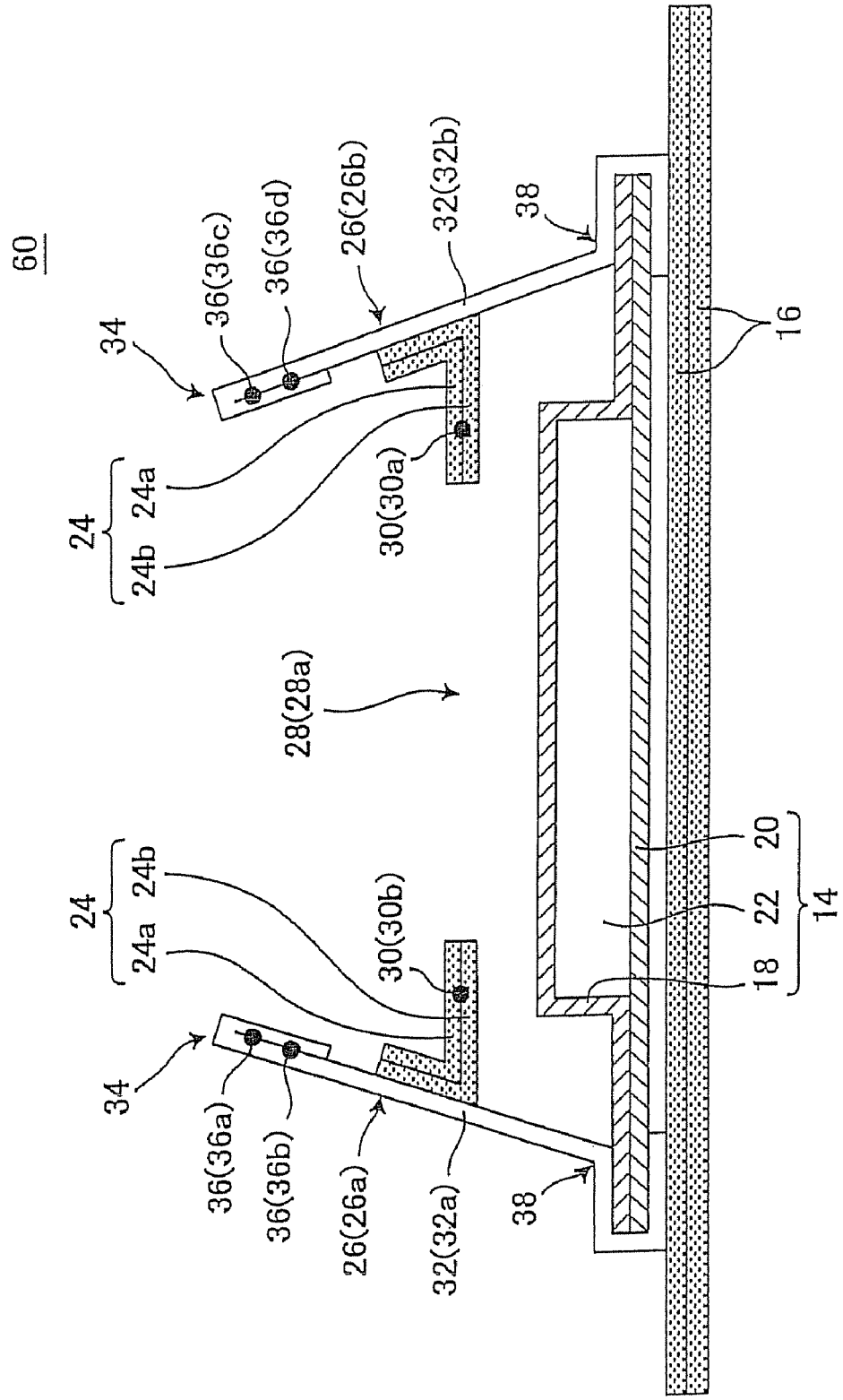
FIG. 4 is a schematic cross-sectional view illustrating the another embodiment of the disposable diaper according to the present invention, as cut the disposable diaper according to the present invention at the part of the stool passing opening in the width direction.
Figure 5:
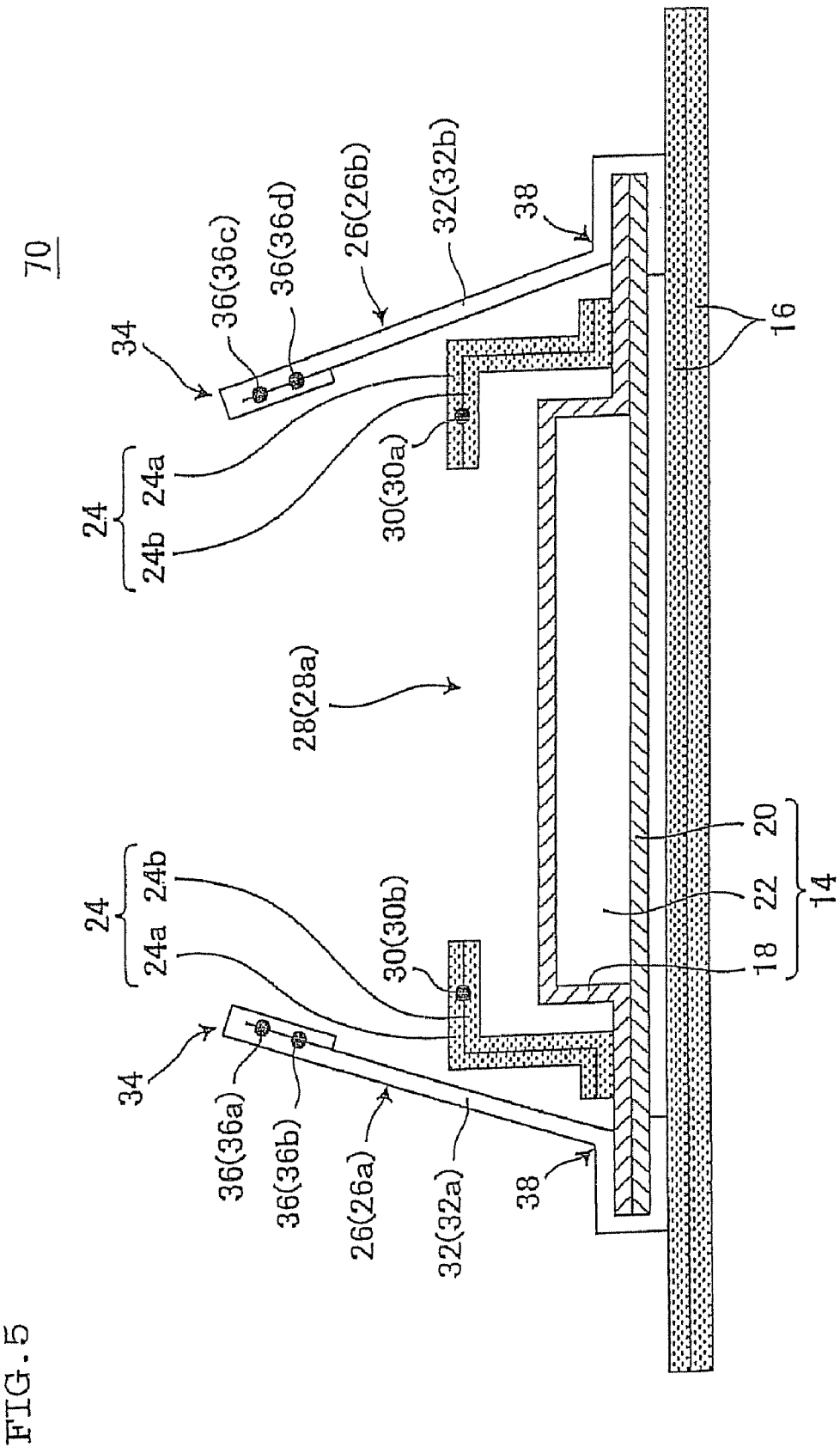
FIG. 5 is a schematic cross-sectional view illustrating still another embodiment of the disposable diaper according to the present invention, as cut the disposable diaper according to the present invention at the part of the stool passing opening in the width direction.
Figure 6:
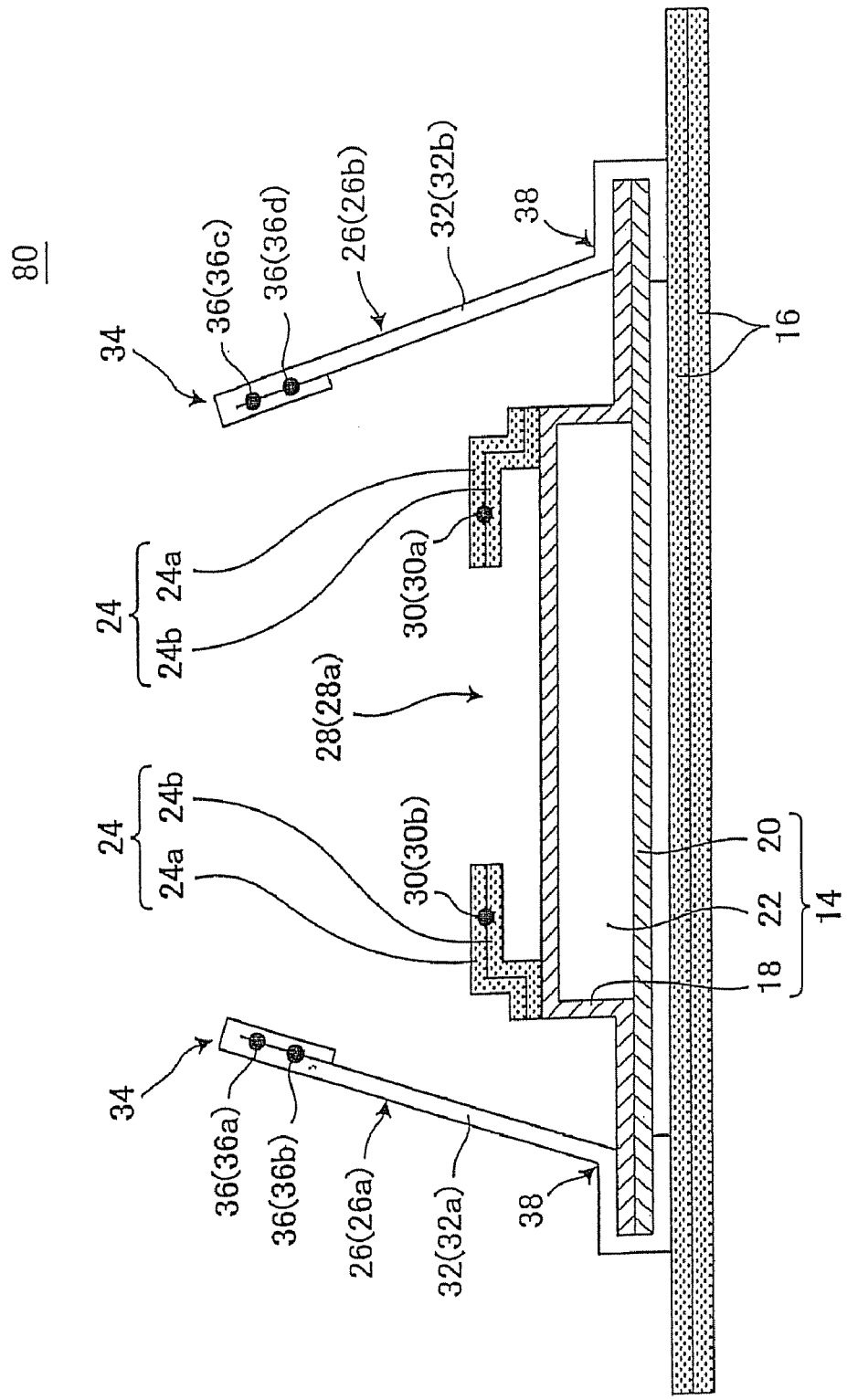
FIG. 6 is a schematic cross-sectional view illustrating still yet another embodiment of the disposable diaper according to the present invention, as cut the disposable diaper according to the present invention at the part of the stool passing opening in the width direction.

The method of fixing the skin contact sheet includes, for example, (1) a method of fixing the skin contact sheet 24 such that the skin contact sheet 24 is inserted in portions where sheet members 32a and 32b, which form standing gathers 26a and 26b, respectively, are pasted with the top sheet 18 (or the back sheet 20), as in the case of the disposable diaper 1 illustrated in FIG. 3, and (2) a method of fixing the skin contact sheet 24 to portions on the inside surfaces of the standing gathers 26a and 26b between upper end edges 34 and lower edges (i.e., standing lines 38) of the standing gathers 26a and 26b, as in the case of a disposable diaper 60 illustrated in FIG. 4.

Alternatively, the skin contact sheet may be fixed in an inside region encompassed by the pair of the standing gathers without being in contact with the standing gathers. For example, there is (3) a method of fixing the skin contact sheet 24 in portions where the top sheet 18 and the back sheet 20 of the absorbent member 14 are pasted together (i.e., so-called flap portions) within the region encompassed by the standing gathers 26a and 26b as in the case of a disposable diaper 70 illustrated in FIG. 5, and (4) a method of fixing the skin contact sheet 24 in portions corresponding to an upper portion of the absorber 22 of the top sheet 18 which constitutes the absorbent member 14 within the region encompassed by the standing gathers 26a and 26b as in the case of a disposable diaper 80 illustrated in FIG. 6.

Further, there is (5) a method of fixing the skin contact sheet 24, in a case in which the absorbent member 14 is formed so that the back sheet 20 protrudes from the lower side of the top sheet 18, within the region encompassed by the standing gathers 26a and 26b, the skin contact sheet 24 can be fixed on both of the top sheet 18 and the back sheet 20 of the absorbent member 14 as in the case of the disposable diaper 90 illustrated in FIG. 7. The method (1) is preferable among the above methods (1) to (5) in that the method is highly effective in making the skin contact sheet in close contact with the skin of the wearer.

[1-2] The standing gathers: The standing gathers are members for preventing the sideward leakage of the urine discharged by the wearer, and are leakage preventing walls structured to stand three-dimensionally. With the provision of the standing gathers, even if the urine is discharged on the skin contact sheet and diffuses down the skin contact sheet, the standing gathers function as breakwaters, and the leakage from the leg-surrounding openings and the like of the diaper (i.e., the so-called sideward leakage) can be effectively prevented.

The standing gather can employ a similar structure to the structure used in the conventional disposable diaper and other absorbent products. For example, by providing a stretchable member (i.e., a standing gather stretchable member) on a part of a sheet member, a gather (i.e., folds) formed on the sheet member by the standing gather stretchable member can be preferably used.

As the material forming the standing gathers, it is preferable to use water-repellent material in a view of increasing the leakage preventing performance of the standing gathers. As the water-repellent material, nonwoven fabrics such as a spunbond, or a card-emboss can be used, however, for the reason of high anti-hydraulic pressure, it is preferable to use nonwoven fabrics such as a SMS (spunbonded/meltblown/spunbonded) or a SMMS (spunbonded/meltblown/meltblown/spunbonded).

The standing gathers can be formed by folding back the top sheet or back sheet of the absorbent member 14 or the skin contact sheet. For example, in the disposable diaper 90 illustrated in FIG. 7, a pair of the standing gathers 26a and 26b is formed by folding back the both side edges of the skin contact sheet 24. More specifically, the disposable diaper 90 is an example that the standing gathers are formed with the folded edges of the skin contact sheet, and the standing gathers are integrally formed with the skin contact sheet. However, it is preferable to form the standing gathers by pasting sheet members which are different from the top sheet, the back sheet, and the skin contact sheet. For example, as in the case of the disposable diaper 1 illustrated in FIGS. 2 and 3, a pair of the standing gathers 26*a* and 26*b* are formed by pasting sheet members 32*a* and 32*b* which are different from the top sheet 18 or the back sheet 20 to portions of both edges of the absorbent member 14.

As the standing gather stretchable member, similar stretchable member to the above-described opening stretchable member can be used. For one standing gather, a single standing gather stretchable member or a plurality of standing gather stretchable members can be arranged. Further, there is no limitation on the position of the arrangement. For example, the standing gather stretchable member can be arranged in the proximity of the lower end edge (i.e., the standing line) of the standing gather or between the upper end edge and the lower end edge (i.e., the standing line) of the standing gather. However, it is preferable to arrange the standing gather in the proximity of the upper end edge of the standing gather.

The disposable diaper 1 illustrated in FIGS. 2 and 3 is an example in which a standing gather stretchable member 36 is arranged in the proximity of the upper end edges of the standing gathers 26*a* and 26*b*. In this example, an edge portion of each of the sheet members 32*a* and 32*b* (i.e., an edge portion corresponding to the upper end edge 34 of each of the standing gather 26*a* and 26*b*) is folded, and the folded portion tucks therein the two standing gather stretchable members 36*a* and 36*b* or the two standing gather stretchable members 36*c* and 36*d*.

With respect to the height of the standing gather (the length from the lower end edge to the upper end edge), it is preferable that the height is to be between 5 mm and 80 mm, and it is more preferable that the height is to be between 10 m and 40 mm. By making the height of the standing gather to be 5 mm or more, sufficient leakage prevention effect can be ensured, and in addition, by making the height to be 80 mm or less, it is possible to prevent a disadvantage that the absorption effect is inhibited because the standing gather covers a surface of the skin contact sheet or the top sheet.

The standing gathers include types, for example, (1) an inside-inclined gather which inclines toward the inside of the diaper, (2) an outside-inclined gather which inclines toward the outside of the diaper, and (3) a standing gather to which a bent part or a folded part is formed at a part in the height direction (a C-folding gather, a Z-folding gather, etc.). Among the above gathers, the inside-inclined gather is preferable. For example, the disposable diaper 1 illustrated in FIGS. 2 and 3 is an example of the inside-inclined gather in which the standing gathers 26*a* and 26*b* are inclined toward the inside.

In order to prevent the side leakage of urine, it is preferable that the standing gathers are formed to the both sides of the skin contact sheet. It is more preferable that the standing gathers are formed along the both side edge parts of the skin contact sheet. By the structure, even if the urine is discharged on the skin contact sheet and diffuses down the skin contact sheet, the standing gathers function as breakwaters, and the sideward leakage from the leg-surrounding openings can be effectively prevented.

For example, the disposable diaper 1 illustrated in FIGS. 2 and 3 is an example in which the skin contact sheets 24 are disposed onto both side edges of the absorbent member 14 and the standing gathers 26*a* and 26*b* are formed on the both side edges of the skin contact sheets 24, that is, along the both side edges of the absorbent member 14. The disposable diaper 1 illustrated in FIGS. 2 and 3 is an example in which the standing gathers 26*a* and 26*b* are formed over the entire of the both side edges, however, in order to prevent the sideward leakage of urine, the standing gathers 26*a* and 26*b* may be disposed at least to the portion corresponding to the crotch part of the disposable diaper.

As in a case of the disposable diaper 90 illustrated in FIG. 7, if the skin contact sheets 24 and the standing gathers 26*a* and 26*b* are integrally formed respectively, the disposable diaper in which the standing gathers 26*a* and 26*b* are formed along the both standing lines 46 of the skin contact sheets 24 has similar effect as "the disposable diaper in which the standing gathers are formed along the both side edges of the skin contact sheet", thus, included in the scope of the present invention. Because original part where functions as the skin contact sheet is the part upper than the standing line, in the case in which the skin contact sheet and the standing gather are integrally formed, the standing line of the skin contact sheet can be considered as the side edge of the skin contact sheet. That is, also in such structured disposable diaper, even if the urine is discharged on the skin contact sheet and diffuses down the skin contact sheet, the standing gathers function as breakwaters, and the sideward leakage from the leg-surrounding openings can be effectively prevented.

It is preferable to form the standing gather into such a structure that the upper end edge of the standing gather is disposed to a position higher than the surface of the skin contact sheet. With the structure, even if the urine is discharged on the skin contact sheet and diffuses down the skin contact sheet, it can be prevented that the urine leaks out over the standing gather.

The method of disposing the upper end edge of the standing gather to a position higher than the surface of the skin contact sheet includes a method of disposing the lower end edge of the standing gather onto the surface of the skin contact sheet. That is, in the disposable diaper according to the present invention, it is preferable to dispose the lower end edge of the standing gather onto the surface of the skin contact sheet. With the structure, the upper end edge of the standing gather is definitely disposed to the position higher than the surface of the skin contact sheet. Then, by adequately adjusting the height of the standing gather depending on the surface height of the skin contact sheet, it is possible to definitely prevent that the urine leaks out over the standing gather.

For example, the disposable diaper 1 illustrated in FIG. 3 is an example in which the skin contact sheets 24 are fixed to the pasted part to be sandwiched between the standing gathers 26*a* and 26*b* and the top sheet 18 respectively so that the lower end edges of the standing gathers 26*a* and 26*b* are disposed on the surface of the skin contact sheet 24 and the upper end edges 34 are disposed to the position higher than the surface of the skin contact sheet 24. In the present specification, the "lower end edge of the standing gather" refers to the fixed end of the standing gathers 26*a* and 26*b*, that is, the part of the standing line 38 as illustrated in FIG. 3.

As in a case of the disposable diaper 90 illustrated in FIG. 7, the method of forming the standing gathers 26*a* and 26*b* by folding the side end side of the skin contact sheet 24 has similar effect to "the method of disposing the lower end edge of the standing gather onto the surface of the skin contact sheet", thus included in the scope of the present invention. Because as in the case of the disposable diaper 90 illustrated in FIG. 7, if the skin contact sheet 24 and the standing gathers 26*a* and 26*b* are integrally formed, it is possible to consider that the lower end edges of the standing gathers 26*a* and 26*b* (standing lines 38) and the surface of the skin contact sheet 24 are continuously formed respectively. That is, also in such structured disposable diaper, by adequately adjusting the height of the standing gather depending on the surface height of the skin contact sheet, it is possible to definitely prevent that the urine leaks out over the standing gather.

In the disposable diaper according to the present invention, at least a pair of standing gathers should be formed, however, more than one pair of the standing gathers may be formed.

[1-3] The absorber: The absorber is a member for absorbing and retaining the urine of the wearer. The absorber is made of an absorbent material due to the need to absorb and retain the urine and the body fluid of the wearer.

The absorbent material forming the absorber includes conventionally known absorbent materials usually used in the disposable diaper and other absorbent products, such as fluff pulp, super absorbent polymer (hereinafter refereed to as SAP), and a hydrophilic sheet, for example. It is preferable to use wood pulp or non-wood pulp fibrillated into floc as the fluff pulp, to use sodium polyacrylate as the SAP, and to use tissue, an absorbent paper, or a hydrophilicized nonwoven fabric as the hydrophilic sheet.

Each of these absorbent materials is usually used in the form of a single-layer mat or a multiple-layer mat. In such a case, a single type of the above absorbent materials may be independently used, or two or more types of the absorbent materials may be used in combination. In particular, it is preferable to use approximately 10 to 500 parts by mass of the SAP with respect to 100 parts by mass of the fluff pulp. In this case, the SAP may be evenly mixed in each of the fluff pulp mats or may be placed in layers between a plurality of fluff pulp layers.

It is preferable that the absorber is interposed between at least parts of the top sheet and the back sheet. Usually, the absorber is sandwiched between the top sheet and the back sheet, and the peripheral rim of the absorber is sealed by adhesion so that the absorber is interposed between the top sheet and the back sheet. Therefore, the flap portions, in which the absorber is not interposed between the top sheet and the back sheet, are formed around the peripheral rim of the absorber.

It is preferable the entire absorber is wrapped by a hydrophilic sheet. This structure provides an advantage in that the SAP is prevented from leaking from the absorber and that the absorber is provided with the shape stability.

There is no particular restriction on the shape of the absorber. The shape of the absorber includes the shapes used in the conventional disposable diaper and other absorbent products, such as a rectangular shape, an hourglass shape, a calabash shape, and a T-shape, for example.

[1-4] The top sheet: The top sheet is a sheet disposed to cover the upper surface of the absorber (i.e., the surface at the side of the skin of the wearer when the diaper is applied to the wearer). The top sheet is at least partially (i.e., a part or the entirety of the top sheet is) made of a liquid permeable material due to the need to cause the absorber disposed at the side of the lower surface of the top sheet to absorb the urine of the wearer.

The liquid permeable material forming the top sheet includes a woven fabric, a nonwoven fabric, and a porous film, for example. In particular, it is preferable to use a hydrophilicized nonwoven fabric made of a thermoplastic resin such as polypropylene, polyethylene, polyester, or nylon.

The top sheet may be formed by a single sheet material. Alternatively, the top sheet may be formed by a plurality of sheet materials. For example, in a frequently used embodiment of a tape-type diaper later described, a top sheet (i.e., a center sheet) made of a liquid permeable material is disposed at the center of the diaper, and another top sheet (i.e., a side sheet) made of a water repellent material is disposed at side flap portions of the diaper.

[1-5] The back sheet: The back sheet is a sheet disposed to cover the lower surface of the absorber (i.e., the surface at the side of the clothes of the wearer when the diaper is applied to the wearer). The back sheet is made of a liquid impermeable material due to the need to prevent the urine of the wearer from leaking to the outside of the diaper.

The liquid impermeable material forming the back sheet includes, for example, a liquid impermeable film made of a resin such as polyethylene. In particular, it is preferable to use a microporous polyethylene film. The microporous polyethylene film is formed with a multitude of micro holes of a size of 0.1 to a few micrometers. The microporous polyethylene film is liquid impermeable but moisture permeable, and thus has an advantage of capable of preventing the inside of the diaper from becoming stuffy.

A sheet member (i.e., a cover sheet) may be pasted to the outer surface of the back sheet. The cover sheet is used to reinforce the back sheet and to improve the hand feeling (i.e., the tactile feeling) of the back sheet.

The material forming the cover sheet includes a woven fabric and a nonwoven fabric, for example. In particular, it is preferable to use a dry or wet nonwoven fabric made of a thermoplastic resin such as polyethylene, polypropylene, or polyester.

[1-6] The absorbent member: In the two-piece-type and pants-type diaper, the top sheet, the back sheet, and the absorber are formed as one member, i.e., the "absorbent member" having the absorbing and retaining function, and the absorbent member is joined with the exterior covering member, which has been manufactured separately from the absorbent member. Thereby, the disposable diaper is formed. In the absorbent member, as in the case of a sanitary napkin or the like, the top sheet and the back sheet are disposed on the upper surface and the lower surface of the absorber, respectively, so that the absorber is interposed between the top sheet and the back sheet. For example, the disposable diaper 1 illustrated in FIG. 3 is an example in which the absorbent member 14 is formed by inserting the absorber 22 between the top sheet 18 and the back sheet 20 and adhering and sealing the peripheral rim of the absorber 22 to make the absorber 22 interposed between the top sheet 18 and the back sheet 20.

The absorbent member is formed into such a size to cover at least the crotch part of the diaper. To ensure the leakage preventing effect, however, it is preferable to form the absorbent member into such a size to cover not only the crotch part but also a part of the front body part and the back body part. The absorbent member can be fixed to the exterior covering member with the hot-melt adhesive agent or the like, for example.

[1-7] The exterior covering member: The exterior covering member is a member having the fitting function of covering the body of the wearer. Specifically, the exterior covering member is a sheet-shaped member for forming respective parts of the front body part, the crotch part, and the back body part.

In the two-piece-type and pants-type diaper, the absorbing and retaining function of absorbing and retaining the excrement of the wearer is performed solely by the absorbent member, and thus there is no need to use the liquid impermeable material as the material forming the exterior covering member. The material forming the exterior covering member includes, for example, a nonwoven fabric formed by a synthetic fiber of polyethylene, polypropylene, polyester, or another thermoplastic resin.

The exterior covering member is fixed, with such members as the leg-surrounding stretchable members inserted in the exterior covering member. In many cases, therefore, the exterior covering member is formed by pasting together two or more nonwoven fabrics. For example, the disposable diaper 1 illustrated in FIGS. 1 to 3 is an example in which the exterior covering member 16 is formed by two nonwoven fabrics, and leg-surrounding stretchable members 40, waist-surrounding stretchable members 42, and belly-surrounding stretchable members 44 are inserted and fixed between the two nonwoven fabrics.

[1-8] The respective stretchable members: In the pants-type disposable diaper, the leg-surrounding stretchable members and the waist-surrounding stretchable members are generally provided, and it is preferable to further provide the belly-surrounding stretchable members.

The leg-surrounding stretchable members are stretchable members placed along the respective leg-surrounding openings. With the provision of the leg-surrounding stretchable members, highly stretchable gathers (i.e., leg gathers) can be formed around the leg-surrounding openings. Accordingly, a clearance gap is not easily formed around the legs, and the leakage of the urine from the leg-surrounding openings can be effectively prevented.

The waist-surrounding stretchable members are stretchable members placed along the waist-surrounding opening. With the provision of the waist-surrounding stretchable members, a highly stretchable gather (i.e., a waist gather) can be formed around the waist-surrounding opening. With the waist gather, a clearance gap is not easily formed around the waist, and the leakage of the urine from the area around the waist can be prevented. Further, the fittedness of the diaper to the wearer is improved, and thus the diaper is prevented from slipping down.

The belly-surrounding stretchable members are stretchable members placed in a portion between the waist-surrounding opening and the leg-surrounding openings (i.e., a portion corresponding to the area around the belly of the wearer). With the provision of the belly-surrounding stretchable members, a highly stretchable tummy gather can be formed around the belly of the wearer. Coupled with the waist gather, the tummy gather can further improve the fittedness of the diaper and the effect of preventing the slide down of the diaper.

The disposable diaper 1 illustrated in FIGS. 1 and 2 is an example in which a plurality of the leg-surrounding stretchable members 40 are placed around the peripheral rims of the leg-surrounding openings 12a and 12b, and a plurality of the waist-surrounding stretchable members 42 are placed around the peripheral rim of the waist-surrounding opening 10 so as to surround the waist-surrounding opening 10. Further, a plurality of the belly-surrounding stretchable members 44 are placed in the portion between the waist-surrounding opening 10 and the leg-surrounding openings 12a and 12b (i.e., the portion corresponding to the area around the belly of the wearer) so as to surround the belly of the wearer.

Each of these stretchable members can employ a similar structure to the structure used in the opening stretchable member described above. Further, the material forming the stretchable member, the elongation rate of the material, the elongated state of the stretchable member when the stretchable member is fixed, and the like can be determined in consideration of such factors as the extent of contraction of the gather.

[2] The manufacturing method: An embodiment of the method of manufacturing the disposable diaper according to the present invention will now be described, taking an example in which the disposable diaper 1 illustrated in FIGS. 1 to 3 (i.e., the two-piece-type and pants-type diaper) is manufactured.

[2-1] The manufacture of the absorbent member: The absorber 22 wrapped by a hydrophilic sheet is disposed on the upper surface of the back sheet 20, and the top sheet 18 is disposed on the upper surface of the absorber 22. Then, the peripheral rim of the absorber 22 is sealed by adhesion, sandwiched by the top sheet 18 and the back sheet 20. Thereby, the absorbent member 14 is obtained.

[2-2] The manufacture of the skin contact sheet: The upper sheet 24a is pasted on the upper surface of the liner sheet 24b, with the two opening stretchable members 30a and 30b arranged in a predetermined pattern. In this case, the two opening stretchable members 30a and 30b are arranged in such a pattern to cross at the point P between the stool passing opening 28a and the urine passing opening 28b, which are later formed, and to surround a part of the peripheral rim of each of the stool passing opening 28a and the urine passing opening 28b.

Subsequently, the stool passing opening 28a and the urine passing opening 28b are formed into respective predetermined shapes on the liner sheet 24b and the upper sheet 24a, which have been pasted together. Thereby, the double-layer structured skin contact sheet 24 is obtained in which the two opening stretchable members 30a and 30b are arranged in such a pattern to cross at the point P between the stool passing opening 28a and the urine passing opening 28b, and to surround a part of the peripheral rim of each of the stool passing opening 28a and the urine passing opening 28b.

[2-3] The manufacture of the standing gathers: One edge portion of the sheet member 32a or 32b is folded, and the two the standing gather stretchable members 36a and 36b or 36c and 36d are tucked in and pasted to the obtained folded portion. Thereby, the standing gather 26a or 26b is obtained.

[2-4] The provision of the skin contact sheet and the like to the absorbent member: The skin contact sheet 24 is pasted to a surface of the top sheet 18 which forms the absorbent member 14, and then each of the standing gathers 26a and 26b is pasted to the corresponding side edge of the absorbent member 14 and the skin contact sheet 24, with each of the standing gathers 26a and 26b tucking therein the corresponding side edge of the absorbent member 14 and the skin contact sheet 24.

[2-5] The manufacture of the exterior covering member: Two nonwoven fabrics for forming the exterior covering member 16 are first prepared. Then, the waist-surrounding stretchable members 42, the belly-surrounding stretchable members 44, and the leg-surrounding stretchable members 40 are disposed and fixed by adhesion on the upper surface of one of the nonwoven fabrics. Thereafter, the other one of the nonwoven fabrics is layered on and fixed to the upper surface of the one of the nonwoven fabrics.

Thereby, the exterior covering member 16 is obtained in which the waist-surrounding stretchable members 42, the belly-surrounding stretchable members 44, and the leg-surrounding stretchable members 40 are interposed between the two nonwoven fabrics.

[2-6] The manufacture of the disposable diaper: The absorbent member 14 is disposed at and fixed to the proximity of the crotch part of the exterior covering member 16. Then, the exterior covering member 16 is folded in half such that the front body part 2 and the back body part 6 are aligned with each other, with the absorbent member 14 on the inside of the folded exterior covering member 16. Thereafter, the front body part 2 and the back body part 6 are joined by such a method as heat-sealing, and the joining parts 8 are formed. Thereby, the disposable diaper 1 illustrated in FIGS. 1 to 3 is manufactured.

The above-described sequence of processes can be continuously performed by a mechanical method or apparatus. For example, with a method or apparatus for continuously sending out a long sheet material or a long stretching material by a roller, for example, the continuous manufacture of the disposable diaper can be performed. This contributes to the improvement of the productivity.

[3] The scope of application of the present invention: The scope of application of the disposable diaper according to the present invention is not limited to the above-described two-piece-type and pants-type diaper, but the present invention is also applicable to a one-piece-type and pants-type diaper and a tape-type diaper, for example. That is, these diapers can also have the effects of the disposable diaper according to the present invention, if the skin contact sheet is disposed above the surface of the top sheet and is formed with the stool passing opening of a predetermined shape.

The phrase "one-piece-type diaper" refers to a type of diaper which includes a top sheet, a back sheet, and an absorber, similarly to the two-piece-type diaper, but in which the absorber having the absorbing and retaining function is interposed (i.e., embedded) between the top sheet and the back sheet and is integrated with the top sheet and/or the back sheet having the fitting function.

The phrase "tape-type diaper" refers to a disposable diaper which includes a top sheet, a back sheet, an absorber interposed between at least parts of the two sheets, and tape fasteners for fitting the diaper, and in which a front body part and a back body part can be fixed to each other by the tape fasteners. The phrase "tape-type diaper" also includes the "one-piece-type" and the "two-piece-type," and the disposable diaper according to the present invention is applicable to either type of the tape-type diaper.

The disposable diaper according to the present invention can be preferably used as the diaper for an infant or an adult such as an elder or disabled person who needs nursing care. Further, in the disposable diaper according to the present invention, a discharged stool does not easily directly contact with the skin of a wearer of the diaper. Accordingly, the disposable diaper according to the present invention can be preferably used particularly as the disposable diaper for an infant who has a sensitive skin and thus frequently has skin trouble.

What is claimed is:

1. A disposable diaper comprising:
an absorbent member comprising an absorber, a top sheet covering an upper surface of the absorber and at least partially formed of a liquid permeable material, and a back sheet covering a lower surface of the absorber and formed of a liquid impermeable material;
a skin contact sheet disposed above the top sheet and having a stool passing opening capable of passing a stool therethrough formed therein; and
a pair of laterally opposed sheet members having standing gathers and being formed of a liquid impermeable material, wherein lower end portions of the sheet members are disposed to wrap around respective lateral side edges of the absorbent member, and wherein an upper surface of the skin contact sheet is laterally located between the sheet members having standing gathers and spaced a distance above the top sheet, and
wherein both side ends of the skin contact sheet and the absorbent member are wrapped with the standing gathers.

2. The disposable diaper according to claim 1, wherein upper end edges of the sheet members having the standing gathers extend a distance above the upper surface of the skin contact sheet.

3. The disposable diaper according to claim 1,
wherein a portion of lower end edges of the sheet members having the standing gathers are disposed on the upper surface of the skin contact sheet.

4. The disposable diaper according to claim 1, wherein a lower surface of folded side edges of the skin contact sheet contact an inner surface of the sheet members having the standing gathers.

5. The disposable diaper according to claim 1, wherein a lower surface of folded side edges of the skin contact sheet contact an upper surface of the top sheet and wherein lateral side edges of the skin contact sheet are spaced a distance from inner surfaces of the sheet members having the standing gathers.

* * * * *